(12) United States Patent
Withiam et al.

(10) Patent No.: US 6,984,377 B2
(45) Date of Patent: *Jan. 10, 2006

(54) ORAL CARE PRODUCTS COMPRISING CALCIUM METASILICATES

(75) Inventors: Michael C. Withiam, Landenberg, PA (US); Donald P. Conley, Conowingo, MD (US)

(73) Assignee: J. M. Huber Corporation, Edison, NJ (US)

( * ) Notice: Subject to any disclaimer, the term of this patent is extended or adjusted under 35 U.S.C. 154(b) by 312 days.

This patent is subject to a terminal disclaimer.

(21) Appl. No.: 10/446,352

(22) Filed: May 28, 2003

(65) Prior Publication Data

US 2004/0013616 A1   Jan. 22, 2004

Related U.S. Application Data

(63) Continuation-in-part of application No. 10/156,890, filed on May 29, 2002, now Pat. No. 6,610,266.

(51) Int. Cl.
*A61K 7/16* (2006.01)

(52) U.S. Cl. .................. 424/49; 424/401; 424/464; 424/465; 424/466; 424/675; 424/682

(58) Field of Classification Search ............... 424/49, 424/401, 464, 465, 466, 675, 682
See application file for complete search history.

(56) References Cited

U.S. PATENT DOCUMENTS

| | | | | |
|---|---|---|---|---|
| 4,038,380 A | * | 7/1977 | Cordon | 424/49 |
| 5,804,165 A | * | 9/1998 | Arnold | 424/44 |
| 2005/0019398 A1 | * | 1/2005 | Kothart et al. | 424/464 |

* cited by examiner

*Primary Examiner*—Frederick Krass
(74) *Attorney, Agent, or Firm*—Carlos Nieves; David Mitchell Goodrich; William Parks

(57) ABSTRACT

Disclosed is an oral care composition comprising a calcium metasilicate having an aspect ratio (average major axial diameter/average minor axial diameter) of from about 1:1 to about 2.5:, and an oil absorption of from about 20 ml/100 g to about 220 ml/100 g. Also disclosed is an oral care composition comprising: a calcium metasilicate having an aspect ratio (average major axial diameter/average minor axial diameter) of from about 1:1 to about 2.5:, and an oil absorption of from about 20 ml/100 g to about 220 ml/100 g, a disintegration aid, an organoleptic enhancing agent, and an abrasive.

11 Claims, 2 Drawing Sheets

ORAL CARE PRODUCTS COMPRISING CALCIUM METASILICATES

This is a continuation in part application of U.S. patent application Ser. No. 10/156,890, filed May 29, 2002 now U.S. Pat. No. 6,610,266 entitled "Calcium Metasilicates and Methods for Making".

BACKGROUND OF THE INVENTION

Many consumer products, such as health and personal care products, are manufactured and packaged in solid, compacted form. The solid, compacted product form has several advantages over other product forms, such as relative ease of manufactures and durability in shipment and convenience in storing for retailers and consumers alike. The tablet solid form is particularly well-suited for over-the-counter prescription pharmaceutical, and nutritional products that are to be administered orally, because virtually any pharmaceutically-active medicament is capable of being granulated and prepared in powdered form without affecting its medicinal effectiveness. Moreover, after being swallowed, the tablets quickly disintegrate within the acidic environment of the stomach, and the active medicament within the tablet is readily digested and absorbed into the blood stream.

However, in certain situations it would be beneficial if the tablet would disintegrate in the mouth so that the active pharmaceutical could be delivered to the blood stream of a patient without the necessity of swallowing the tablet. For example, children and advanced geriatric patients (those over 80 years old) often have difficulty swallowing pills, and a tablet that dissolves or rapidly disintegrates in the mouth would provide a convenient and effective solid form delivery system for such patients. Additionally, a tablet that dissolves, or disintegrates, in the mouth would be helpful for mentally disabled individuals who require treatment with pharmaceuticals, but refuse to swallow tablets.

Yet another situation where oral disintegration would be helpful is where water may not be readily available to assist in swallowing the tablet, such as when a person is traveling in an automobile or under certain working conditions.

Unfortunately, most tablets do not readily dissolve in the mouth, but instead disintegrate in a slow and uneven fashion, so that if the tablet is not swallowed, then a dosage significantly below the therapeutically effective level will be delivered to the bloodstream. This is particularly serious when a pharmaceutical tablet is administered to treat a bacterial disease, and the refusal of a patient to swallow the tablet results in a sub-therapeutically effective amount of an antibiotic being delivered to the bloodstream, allowing the bacteria to develop resistance to the antibiotic. Given the forgoing there is a continuing need for solid form pharmaceutical preparations that rapidly disintegrate. Particularly needed are tablet compositions that readily disintegrate in the mouth, and thereby eliminate the need for the tablet to be swallowed.

BRIEF SUMMARY OF THE INVENTION

The present invention includes an oral care composition containing a calcium metasilicate having an aspect ratio (average major axial diameter/average minor axial diameter) of from about 1:1 to about 2.5:1, and an oil absorption of from about 20 ml/100 g to about 220 ml/100 g.

The invention also includes an oral care composition comprising: a calcium metasilicate having an aspect ratio (average major axial diameter/average minor axial diameter) of from about 1:1 to about 2.5:1, and an oil absorption of from about 20 ml/100 g to about 220 ml/100 g; a disintegration aid, an organoleptic enhancing agent, and an abrasive.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments that are presently preferred. It should be understood, however, that the invention is not limited to the precise arrangements and instrumentalities shown. In the drawings.

DETAILED DESCRIPTION OF THE INVENTION

Figure 1:
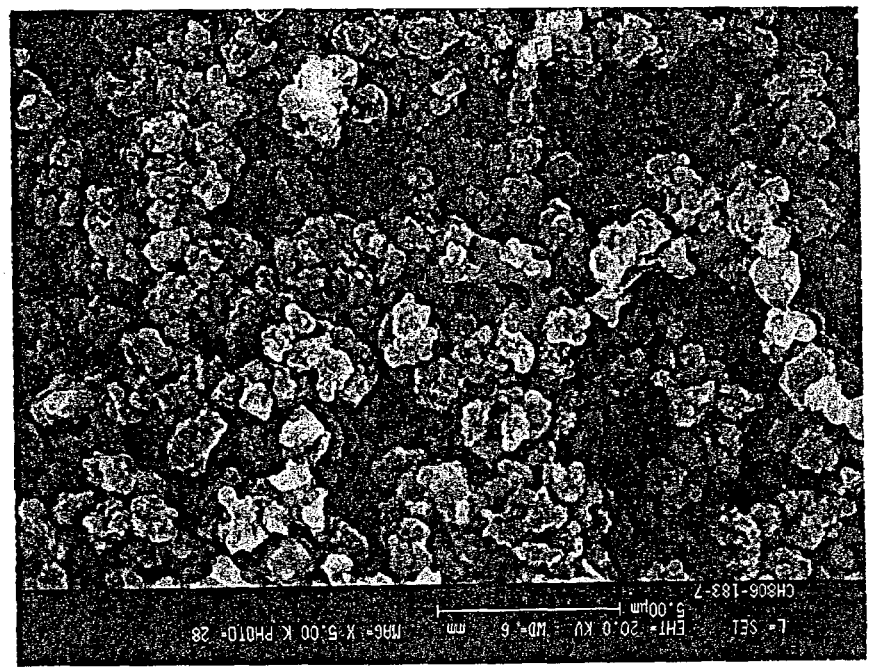
FIG. 1 is an SEM Micrograph of the calcium metasilicate material prepared in Example 1, below.

All parts, percentages and ratios used herein are expressed by weight unless otherwise specified. All documents cited herein are incorporated by reference.

By "mixture" it is meant any combination of two or more substances, in the form of, for example without intending to be limiting, a heterogeneous mixture, a suspension, a solution, a sol, a gel, a dispersion, or an emulsion.

The present application relates to synthetic calcium metasilicate useful as an additive in pharmaceutical, food, agricultural, personal care, home care and like products, which when incorporated in a solid, formed product (e.g., a tablet) significantly increases the disintegration rate of the formed product, when contacted by a substantially aqueous environment (such as mammalian saliva or mucous). While not wishing to be limited by theory, it is believed that calcium metasilicates prepared according to the present invention provide this enhanced disintegration performance because of their high oil absorption and low aspect ratio. In particular, the high oil absorption indicates that the calcium metasilicates absorb high amounts of water, while the low aspect ratio means that the calcium metasilicates form an interlocking structure with a high intraparticle void volume. Thus, water is absorbed by the calcium metasilicates and penetrates into the particle voids to push apart the particles of the solid product. The present calcium metasilicates are particularly effective at enhancing the rate of disintegration of tablet compositions that contain one or more disintegrants, because as the calcium metasilicate provides the initial separation and untangling of adjoining particles, the disintegrants then provide a more substantial disintegrating effect to the separated particles.

The present calcium metasilicates are particularly suitable for pharmaceutical product preparations prepared in solid form and meant to be orally administered. When included in such products, the tablet readily disintegrates in the mouth, and thus eliminates the need for swallowing whole tablets. Also, these calcium metasilicates are useful not only in tablets meant for human consumption, but may also be particularly useful in veterinary pharmaceuticals for pets as many pets have acquired the reputation of being somewhat reluctant to swallow solid formed pharmaceutical preparations.

Additionally, these calcium metasilicates are useful in products which may be in forms other than tablets, such as certain solid formed food products, such as bouillon cubes, yeast cakes and the like; agricultural products such as herbicides, fungicides, pesticides, and fertilizers; and personal and home care products such as bath granules, fragrance, soap, and shampoo products for camping or boating, where carrying aqueous solutions is inconvenient, and automatic dishwashing detergents laundry detergent, toilet bowl cleaners and the like.

Calcium metasilicates prepared according to the present invention, as well as methods for making them, will now be discussed in detail. Then products incorporating these ingredients, particularly solid, formed pharmaceutical preparations will be discussed and examples of such products provided.

Calcium metasilicate ($CaSiO_3$) is used to describe materials that are characterized by a ratio of moles of calcium to mole of silicon, of about 1.0. Naturally occurring mineral forms of the material range from about 0.8 to 1.3 $CaO/SiO_2$ molar ratio. More commonly, and specifically, the term calcium metasilicate is used to describe the various types of minerals and synthetic (amorphous and crystalline) materials chemically-resembling wollastonite. It is accepted that wollastonite minerals occur in three crystalline types, type 1A, 2M and 7M, but type 1A is the only prevalent form of wollastonite with types 2M, and 7M being very rare, and typically not naturally occurring in nature. Details of types 1A, 2M, and 7M are given below in Table I.

TABLE I

Common Species of Calcium Metasilicate

| Species | Common name | Crystal species | Occurrence |
| --- | --- | --- | --- |
| 1A | Wollastonite | Triclinic | Common |
| 2M | Parawollastonite | Monoclinic | Very rare |
| 7M | Pseudowollastonite | Triclinic | Very rare |

Naturally-occurring calcium metasilicate is mined at many different sites throughout the world. After being mined, the calcium metasilicate is beneficiated to yield various grades, and depending on its specific grade, used in a variety of industrial applications such as rheology modifiers and structural additives. These naturally-occurring calcium metasilicates have a crystalline form and high aspect ratios (above 3:1, and in some case above even above 20:1), that provides rigidity and strength. Properties of commonly available naturally-occurring mined wollastonite are given in Table II below.

TABLE II

Properties of Mined, Naturally-occurring, Commercially Available Wollastonite.

| Wollastonite Product | Density g/cc | Crystal Morphology | Crystal Aspect ratio | Oil Absorption ml/100 g | Brightness % |
| --- | --- | --- | --- | --- | --- |
| VANSIL W10 | 0.29 | acicular | >3:1 | 19 | 80 |
| READE 400 Powder | 0.39 | acicular | >3:1 | 45 | 89 |
| BOUD GRADE 2RF | 0.37 | acicular | 20:1 | 40 | 65 |
| BOUD GRADE W4 | 0.77 | — | 3:1 | 28 | 75 |

In addition to the naturally occurring calcium metasilicates, calcium metasilicates may also be produced synthetically for use in specialty ceramics and materials research. However, these calcium metasilicates are not crystalline, but rather have a glassy or amorphous microstructure. Moreover, the poor oil absorption performance of synthetic calcium metasilicates, which have about half the oil absorption capacity as naturally occurring calcium metasilicates (shown in Table III, below), indicates that synthetic calcium metasilicates have a rather low intraparticle void volume.

TABLE III

Physical properties of synthetically produced calcium metasilicates.

| calcium silicate | Morphology | Oil Absorption, cc/100 g | Surface Area BET, $m^2/g$ | Brightness, % |
| --- | --- | --- | --- | --- |
| ALDRICH | Amorphous, Glassy irregular | 8 | 2 | 84 |
| CERAC | Mixed glassy and porous irregular | 10 | 2 | 85 |

In contrast to either the naturally-occurring or synthetic calcium metasilicates discussed above, the inventive calcium metasilicates disclosed in the present application have a low aspect ratio, and form structured aggregates of uniform particles yielding high oil or water absorption characteristics. Specifically, this low aspect ratio (average major axial diameter/average minor axial diameter) of the calcium metasilicate is between about 1:1 to about 2.5:1, preferably from about 1:1 to about 1.5:1, and they have an oil absorption of from about 20 ml/100 g to about 220 ml/100 g, preferably from about 20 ml/100 g to about 100 m/100 g. (The techniques for measuring aspect ratio and oil absorption are discussed in greater detail below. The major axis is perpendicular, although not necessarily coplanar, with the minor axis.) Preferably the calcium metasilicate is dehydrated (or "calcined").

Calcium metasilicate is itself formed by the reaction of a silica source with a calcium source. The silica source can be selected from naturally occurring pure forms of crystalline silicon dioxide or from synthetic amorphous silicon dioxide. The preferred form of silica is amorphous silicon dioxide, such as precipitated silica, silica gel, fumed silica or colloidal silica as described in USP/NF Monographs entitled, "Dental-Type Silica, Silicon Dioxide and Colloidal Silicon Dioxide." The calcium source may be selected from the group including, silicates, oxides, carbonates, sulfates, hydroxides and salts or mixtures thereof. The preferred source of calcium is calcium hydroxide.

When mixed together, the $CaO/SiO_2$ ratio is between about 0.75 and 1.3, preferably between about 0.95 and 1.05. By the present invention, it has been discovered that by maintaining the $CaO/SiO_2$ mole ratio during mixing in the proximity of about 1:1 (such as in the aforementioned ranges), crystalline silica formation is prevented during subsequent high-temperature dehydration.

Mixing of the silica and calcium sources should continue until a homogeneous mixture is formed. Preferably the calcium and silica sources are combined with sufficient water to provide an easily mixed suspension of the materials.

Once a homogenous mixture is obtained, it can be dried to remove any excess water. Then the mixed solids-homogenous mixture (either dried or undried) is dehydrated (or "calcined") at temperatures of between about 600° C. and about 1200° C., preferably 700° C. to 900° C., for a time period of between 10 and 120 minutes, preferably between about 10 to 60 minutes.

In an especially preferred embodiment of the present invention, milk of lime (calcium hydroxide) slurry is combined with a suspension of amorphous silica in a well-agitated vessel to yield homogeneous mixed solids having a $CaO/SiO_2$ molar ratio between 0.95 and 1.05. The homogenous mixed solids are removed from the vessel and dried in an atomizing spray dryer to obtain a powder in which a substantial portion of the particulates have a size less than 300 μm. The particulates are then calcined in an indirect heated fluid bed calciner at 800° C. for 10 to 60 minutes, preferably 10–30 minutes, and recovered as fine particle wollastonite aggregates. The recovered particulates may optionally be comminuted to finer particle sizes, by any conventional means.

The present calcium metasilicates are included in solid, formed pharmaceutical preparations along with one or more pharmaceutically active ingredients. Suitable pharmaceutically active ingredients include, without intending to be limiting, phospho diesterase inhibitors (PDE-5), nourishing and health-promoting agents, antipyretic, analgesic, antiinflammatory agents, antipsychotic drugs, antianxiety drugs, antidepressants, hypnotic-sedatives, spasmolytics, central nervous system affecting drugs, cerebral metabolism ameliolators, antiepileptics, sympathomimetic agents, gastrointestinal function conditioning agents, antacids, antiulcer agents, antitussive-expectorants, antiemetics, respiratory stimulants, bronchodilators, antiallergic agents, dental buccal drugs, antihistamines, cardiotonics, antiarrhythmic agents, diuretics, hypotensive agents, vasoconstrictors, coronary vasodilators, peripheral vasodilators, antihyperlipidemic agents, cholagogues, antibiotics, chemotherapeutic agents, antidiabetic agents, drugs for osteoporosis, skeletal muscle relaxants, antidinics, hormones, alkaloid narcotics, sulfa drugs, antipodagrics, anticoagulants, anti-malignant tumor agents, agents for Alzheimer's disease, erectile dysfunction, etc. and therapeutically appropriate combinations thereof. These calcium metasilicates may also be included in veterinary pharmaceutical preparations.

These solid formed pharmaceutical preparations may also include one or more disintegration aids, including disintegration aids commonly referred to as super disintegrants. Preferably the disintegration aids act by swelling or wicking in of water. Suitable disintegrants include natural, modified or pregelatinized starch, especially sodium starch glycolate; natural or chemically-modified cellulose, especially crosslinked sodium carboxymethyl cellulose (croscarmellose sodium), and microcrystalline cellulose; gum, especially agar gum, and guar gum; alginic acid or salts thereof; acetates and citrates; sugars (especially sucrose, lactose, mannitol and sorbitol); aluminum oxide; dicalcium phosphate; synthetic polymers such as crospovidone, as well as effervescent disintegrating systems. Typical levels of disintegration aids in the inventive pharmaceutical preparations are from about 0.5% to about 15% of the formulation, by weight.

As discussed above, the present calcium metasilicates may be used in a variety of different solid, formed pharmaceutical products, especially the tablet form. Tablets are prepared by combining the above ingredients, present at different concentration levels, in a homogeneous mixture. The tablets are then manufactured by using a tableting compacting process. A standard single stroke or a rotary press may be used. The tablets prepared according to this invention may be of any shape, such as round or caplet-shaped, and of any size suitable for human or animal use.

The calcium metasilicates disclosed in the present application may also be used in other personal care, home care, agricultural and food products. Examples of personal care products in which the calcium metasilicates may be included are oral care products such as dentifrices, toothpastes, and breath-fresheners.

The oral care products of the present invention typically contain from about 1 wt % to about 50 wt % calcium metasilicate, preferably from about 20 wt % to about 40 wt %. In addition to the aforementioned calcium metasilicates, the oral care products of the present invention may also include several other ingredients such as disintegration aids, organoleptic enhancers, abrasives, thickening agents, (also sometimes known as thickeners, binders, gums, or stabilizing agents), therapeutic agents, and preservatives. Preferably, the oral care products of the present invention will comprise calcium metasilicates, disintegration aids, abrasives, organoleptic enhancers, and thickening agents.

Suitable disintegration aids, and combinations of one or more said disintegration aids, as listed above are present in the oral care products typically at a level from about 0.5 wt % to about 15 wt %, and preferably from about 1 wt % to about 5 wt %.

The inventive oral care compositions may also contain one or more organoleptic enhancing agents. Organoleptic enhancing agents include humectants, sweeteners, surfactants, flavorants, colorants and effervescing agents.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, maltitol, mannitol, lactitol, and hydrogenated starch hydrolyzates, as well as mixtures of these compounds. Typical levels of humectants are from about 0 wt. % to about 30 wt. % of the inventive dentifrice composition.

Sweeteners may be added to the dentifrice composition to impart a pleasing taste to the product. Suitable sweeteners include saccharin (as sodium, potassium or calcium saccharin), cyclamate (as a sodium, potassium or calcium salt), aspartame, acesulfane-K, thaumatin, neohisperidin dihydrochalcone, ammoniated glycyrrhizin, dextrose, maltodextrin, sucralose, fructose, levulose, sucrose, mannose, and glucose. Typical levels of sweeteners are from about 0 wt % to about 5 wt % of a dentifrice composition.

Surfactants are used in the compositions of the present invention to achieve increased prophylactic action and render the dentifrice compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, and the sodium, potassium, and ethanolamine salts of N-lauroyl, N-myristoyl, or N-palmitoyl sarcosine. Sodium lauryl sulfate is a preferred surfactant. The surfactant is typically present in the dentifrice compositions of the present invention in an amount of about 0.3 to about 15% by weight, preferably about 1 to about 10% by weight.

Flavoring agents optionally can be added to dentifrice compositions. Suitable flavoring agents include oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents consist chemically of mixtures of aldehydes, ketones, esters, phenols, acids, and aliphatic, aromatic and other alcohols.

Colorants may be added to improve the aesthetic appearance of the product. Suitable colorants are selected from colorants approved by appropriate regulatory bodies such as the FDA and in the European Food and Pharmaceutical Directives.

The oral care product may also contain an effervescent agent to provide aesthetic properties to the tablet. Preferably effervescence is provided by reaction of a carbonate salt such as calcium carbonate, sodium carbonate and sodium bicarbonate with an acid such as citric acid or malic acid.

Suitable abrasives include precipitated and ground calcium carbonate, precipitated silica, silica gel, calcium metasilicate, dicalcium phosphate dihydrate, calcium pyrophosphate, tricalcium phosphate, alumina, and other suitable abrasive materials known to a person of ordinary skill in the art. The abrasive may be used alone or in combination with other abrasives. Typical levels of abrasives in the inventive dentifrice formulation are from about 10 wt % to about 40 wt %.

Thickening agents or binders are useful in the dentifrice compositions of the present invention to provide a gelatinous structure that stabilizes the dentifrice against phase separation and provides an aesthetically pleasing texture when the composition disintegrates in the mouth. Suitable thickening agents include silica thickener, starch, glycerite of starch, gum karaya (sterculia gum), gum tragacanth, gum arabic, gum ghatti, gum acacia, xanthan gum, guar gum, veegum, carrageenan, sodium alginate, agar-agar, pectin, gelatin, cellulose, cellulose gum, carboxymethyl cellulose, hydroxyethyl cellulose, hydroxypropyl cellulose, hydroxymethyl, hydroxymethyl carboxypropyl cellulose, methyl cellulose, ethyl cellulose, sulfated cellulose, as well as mixtures of these compounds. Typical levels of binders are from about 0 wt % to about 15 wt % of a dentifrice composition.

Therapeutic agents are optionally used in the compositions of the present invention to provide for the prevention and treatment of dental caries, periodontal disease and temperature sensitivity. Examples of therapeutic agents, without intending to be limiting, are fluoride sources, such as sodium fluoride, sodium monofluorophosphate, stannous fluoride and the like; condensed phosphates such as tripolyphosphates and, pyrophosphates; antimicrobial agents such as triclosan, bisguanides, such as alexidine, chlorhexidine and chlorhexidine gluconate; quarternary ammonium compounds, such as benzalkonium chloride (BZK), benzethonium chloride (BZT), cetylpyridinium chloride (CPC), and domiphen bromide; metal salts, such as zinc citrate zinc chloride, and stannous fluoride; sanguinaria extract and sanguinarine; volatile oils, such as eucalyptol, menthol, thymol, and methyl salicylate; amine fluorides; peroxides and the like. Therapeutic agents may be used in dentifrice formulations singly or in combination at a therapeutically safe and effective level.

Preservatives may be also be optionally added to the compositions of the present invention to prevent bacterial growth. Suitable preservatives approved for use in oral compositions such as methylparaben, propylparaben and sodium benzoate may be added in safe and effective amounts.

The oral care products may additionally contain other optional ingredients typically used in tablet making such as anticaking agents to provide even flow of the tableting mixture to the tableting press such as amorphous silica and die release aids, such as magnesium stearate, to enable tablets to be released form the tablet machine die faces.

The invention will now be described in more detail with respect to the following, specific, non-limiting examples.

EXAMPLE 1

A commercial scale embodiment of the process for preparing calcium metasilicate according to the present invention is as follows. In a first step of this example, reactive silica slurry suitable for use in the production of calcium metasilicate was prepared by adding sulfuric acid to a dilute waterglass solution in a well-agitated mixing vessel to affect the precipitation of amorphous hydrated silica. Specifically, a total of 2850 gallons of sulfuric acid at a concentration of 11.5% was added at a rate of 37.4 gpm to 5096 gallons of waterglass solution (3.3 $SiO_2/Na_2O$ mole ratio) containing 13% sodium silicate solids while mixing at a temperature of 95° C. The addition of the sulfuric acid was continued until a pH of 5.5 was obtained, and the reaction mixture was digested for 30 minutes. The resulting suspension of silica particles was recovered by filtration with washing.

Figure 2:
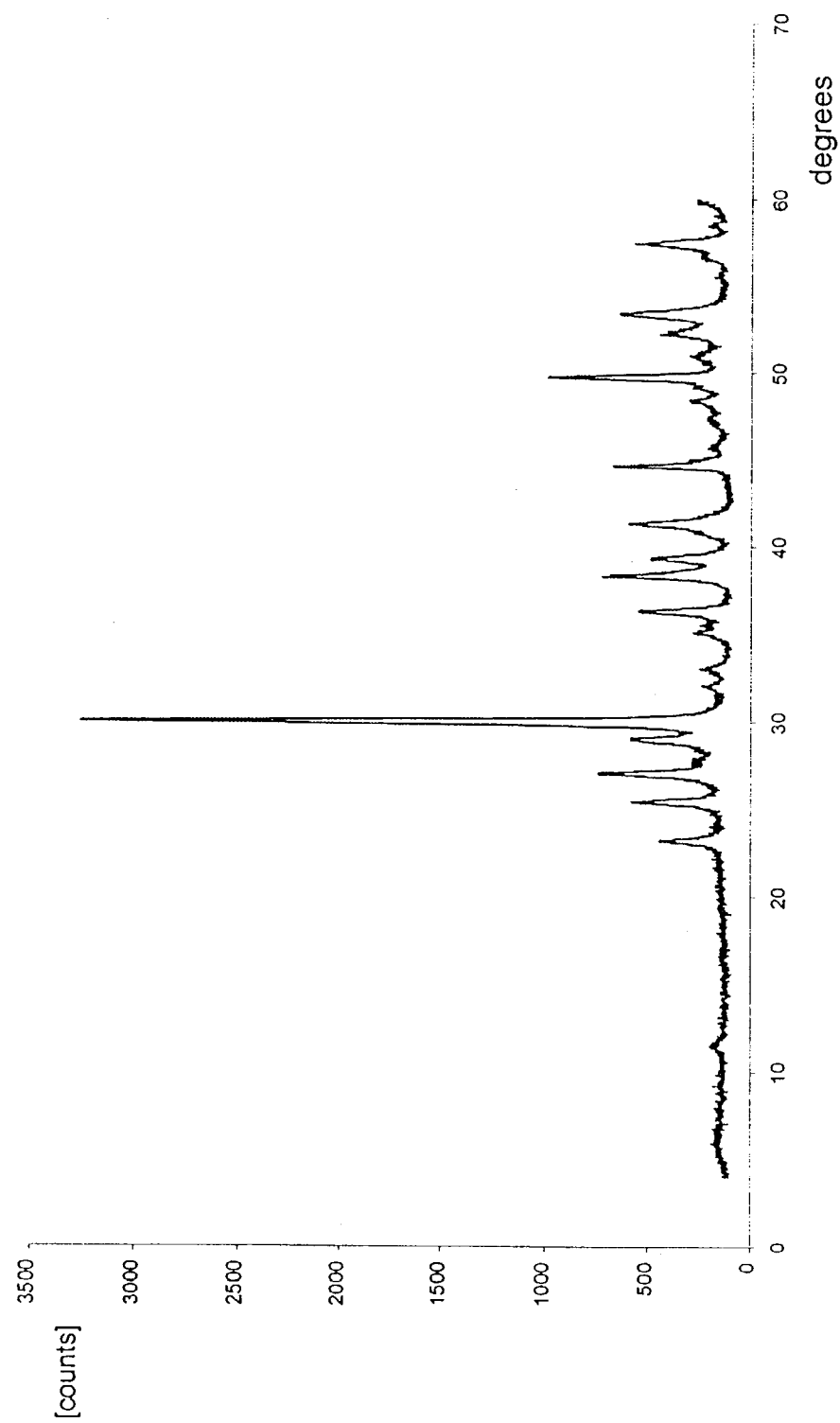
FIG. 2 is an X-ray diffraction pattern of the calcium metasilicate prepared in Example 1, below.

Next, 4688 pounds (approximately 2131 kg) of an aqueous slurry of reactive silica prepared above (with 15.2% solids) was added to a stirred vessel at 40° C. Then, 424 gallons (approximately 1611 liters) of milk of lime slurry (with 20% solids) was added at a rate of 25 gallons per minute (approximately 95 liters per minute). Mixing was continued for 20 minutes, to attain an intimately mixed homogenous suspension. This suspension was dewatered using a rotary vacuum filtration device and dried in an atomizing spray drier. The recovered fine particle size dried powder was then calcined in an indirect gas fired fluid bed calciner for 30 minutes at 800° C. The recovered fine particle size calcium metasilicate was analyzed by powder x-ray diffraction. A $\theta/2\theta$ type diffractometer equipped with a x-ray tube having a copper anode was used. The diffraction scan obtained from this analysis is shown in FIG. 2. This scan indicates the presence of wollastonite 2M, with no traces of crystalline silica. Properties of Example 1 calcium metasilicate are given in Table IV, below.

TABLE IV

Physical and Crystallographic Properties of Calcium Metasilicate Prepared in Example 1

| Product | Density g/cc | Morphology | $CaO/SiO_2$ Molar ratio | Aspect ratio | Oil Absorption ml/100 g | BET Surface Area, $m^2/g$ | Brightness % |
|---|---|---|---|---|---|---|---|
| Example 1 | 0.39 | Wollastonite 2M monoclinic | 0.85 | 1:1 | 70 | 6 | 86 |

The oil absorption shown in Table IV was measured with the rubout method. In this test, linseed oil is mixed with a powdered sample and rubbed with a spatula on a smooth surface until a stiff putty-like paste is formed. By measuring the quantity of oil required to have a paste mixture, which will curl when spread out, one can calculate the oil absorption value of the metasilicate, the value which represents the volume of oil required per unit weight of metasilicate to completely saturate the metasilicate absorptive capacity. Calculation of the oil absorption value was done according to equation (I):

$$\text{Oil absorption} = \frac{\text{ml oil absorbed}}{\text{weight of sample, grams}} \times 100 \quad (1)$$

$$= \text{ml oil/100 grams sample}$$

The aspect ratio given in Table IV is the average major axial diameter/average minor axial diameter, and can be measured as follows. First, samples of the calcium metasilicate material are ground to obtain separate individual particles. This material is dispersed in isopropanol to allow preparation of specimens with unagglomerated individual particles. The specimen is carbon coated before being imaged using standard Scanning Electron Microscopy. SEM micrographs are made at a magnification of 1000× on 77 mm×114 mm images digitized using either a direct digital image capture or through the use of a flat bed scanner. The digital micrographs are evaluated using ImagePro Plus 3.0 software. Images are converted to 2 color high contrast digital images using a threshold pixel gray value of 140. An individual pixel in an image is approximately 0.162 microns in width and height. The calcium metasilicate particle aspect ratio is measured using image analysis to calculate particle width and particle length using the particle information. A histogram of aspect ratio allows the prominent aspect ratio to be determined. A minimum of 100 measurements are made, to assure statistical significance.

The BET surface area in Table IV was determined by the BET nitrogen absorption method of Brunaur et al., as reported in the J. Am. Chem. Soc. 60, 309 (1938), after degassing the sample for 40 minutes at 240° C.

The brightness of the powder sample prepared in Example 1 was measured using a Technidyne Brightmeter S-5/BC according to TAPPI test methods T452 and T646, and ASTM Standard D985. The Technidyne Brightmeter has a dual beam optical system where the sample is illuminated at an angle of 45°, and the reflected light viewed at 0°. The powdered materials are pressed to about a 1 cm thick pellet with enough pressure to give a pellet surface that is smooth and flat and without loose particles or gloss.

To demonstrate their efficacy in solid compacted oral care compositions, the calcium metasilicate material of the present invention, as prepared in Example 1 above, was incorporated into several different example oral care compositions, and the compositions formed into tablets. The specific compositions for the tablets prepared from examples 2–6 are set forth below in Table VI.

EXAMPLE 2

The oral care composition contained 10 g of the calcium metasilicate of Example 1, 1 g SGG and 10 g powdered sucrose. The blend was mixed until homogeneous in a PK-V blender (twin shell dry blender model 014-215-0053, available from Patterson Kelly, East Stroudsburg, Pa.). A portion of the resulting mixture was pressed at 2000 psi in an Angstrom tablet press to obtain 13 mm diameter circular tablets weighing approximately 0.3 g each.

TABLE V

Oral Care Composition Ingredients

| Ingredient | Tradename | Manufacturer |
| --- | --- | --- |
| Calcium carbonate | HUBER-CAL ®500 | J. M. Huber Corporation, Edison, NJ |
| Silica abrasive | ZEODENT ® 113 | J. M. Huber Corporation, Edison, NJ |
| Microcrystalline cellulose (MCC) | AVICEL 101 | FMC Biopolymers, Philadelphia, PA |
| Sodium starch glycolate (SGG) | EXPLOTAB | Penwest Pharmaceuticals, Patterson, NY |
| Carboxymethyl cellulose (CMC) | CMC 7MFX | Hercules Corporation, Aqualon Division, Wilmington, DE |

EXAMPLE 3

To further demonstrate the usefulness of the calcium metasilicates prepared according to the present invention, the calcium metasilicates were incorporated along with additional oral care formulation ingredients commonly used in toothpaste formulations that were not included in Example 2, above. The formulation was prepared by mixing 89 g of Example 1 calcium metasilicate, 1.4 g glycerin (99% solution), 7.9 g calcium carbonate and 29 g MCC until a homogeneous wet mass was achieved. The wet mass was oven dried for 2 hours at 105° C., then milled to a finely divided powder in a lab mill. The recovered milled powder was mixed with 10 g SGG, 2 g dry sodium saccharine and 1.34 g sodium lauryl sulfate in a PK-V blender, then pressed into 13 mm tablets weighing about 0.4 g on a single pellet Angstrom press at 5000 psi.

EXAMPLE 4

Oral care tablets comprising several common oral care formulation ingredients were produced by first combining 178 g calcium metasilicate of Example 1, 58 g MCC in a Hobart mixer and then slowly adding 100 g of a 0.2% aqueous solution of CMC over about a 4-minute period. The resulting homogenous granulated mixture was oven dried at 105° C. for 2 hours, then passed through screens to recover material between 20 and 80 mesh. 11.8 g of the screened mixture (3.51 wt %) was combined with 7.9 g calcium carbonate, 1.1 g sodium lauryl sulfate, 1.0 g SGG and 0.2 g dry sodium saccharine. Tablets weighing 400 mg were made using an Angstrom press fitted with a 13 mm die.

EXAMPLE 5

Oral care tablets comprising several common oral care formulation ingredients were prepared by mixing 2.48 g sodium lauryl sulfate, 0.2 g sodium saccharine, 7.9 g calcium carbonate and 2.9 g MCC, then adding 1.4 g aqueous glycerin solution (99.5%) to form a wet mass. To this mass was added 8.9 g Example 1 calcium metasilicate and 1 g SGG with mixing to form a dry homogenous granular mixture. Then 1.25 g of peppermint flavor was mixing into the granular mixture. The dry flavored mixture was lightly milled for 60 seconds in a Waring coffee mill to completely mix and homogenize the mixture. Tablets were formed by pressing the resulting mixture in an Angstom press fitted with a 13-mm die at 4000 psi. The tablets weighed about 0.6 g.

EXAMPLE 6

Oral care tablets were prepared by combining 30.8 g of a 99.5% aqueous solution of glycerin with 63.86 g MCC in a PK-V blender. Then, 4.4 g sodium saccharine and 25.74 g sodium lauryl sulfate were added and mixed for 20 minutes. SGG (22 g) and 195.8 g Example 1 calcium metasilicate were separately blended together, then added to the PK blender and mixed together with the other ingredients for 5 minutes. Finally, 7 g dry peppermint flavor was added to the blender and all ingredients were mixed together for 10 minutes. Tablets were formed from the resulting formulation on a 4-station Piccola available from Riva S.A., Argentina rotary tablet press fitted with a 11.75 mm concave die over a range of compression forces. A compression force of between 10 kN and 20 kN provided 5 mm thick tablets with adequate integrity.

TABLE VI

| | Tablet % Composition | | | | |
|---|---|---|---|---|---|
| | Ex. 2 % | Ex. 3 % | Ex. 4 % | Ex. 5 % | Ex. 6 % |
| Ex. 1 calcium metasilicate | 47.6 | 35.8 | 26.6 | 34.2 | 37.4 |
| AVICEL 101 MCC | 0 | 11.7 | 8.7 | 11.1 | 12.2 |
| HUBERCAL ® 500 $CaCO_3$ | 0 | 31.8 | 33.6 | 30.3 | 33.2 |
| Sodium lauryl sulfate | 0 | 5.4 | 4.7 | 9.5 | 4.9 |
| EXPLOTAB SSG | 4.8 | 4.0 | 4.3 | 3.8 | 4.2 |
| saccharine | 0 | 0.8 | 0.9 | 0.8 | 0.8 |
| glycerin | 0 | 5.6 | 0.0 | 5.4 | 5.9 |
| CMC 7MFX | 0 | 0.0 | 14.9 | 0.0 | 0.0 |
| sucrose | 47.6 | 0.0 | 0.0 | 0.0 | 0.0 |
| Flavor | 0 | 5.0 | 6.3 | 4.8 | 1.3 |
| total, % | 100 | 100 | 100 | 100 | 100 |

COMPARATIVE EXAMPLES 1 and 2

Oral care tablets were formed as in Example II of WO 99/33437 without the non-essential ingredients: color, sodium fluoride, cetyl pyridinium chloride and flavor. Since this patent application was silent as to the compression forces used to form the tablets, several different compression forces were used for tablet formation. Tablets were formed by pressing the resulting mixture in an Angstrom press fitted with a 13-mm diameter die at 2000 psi, 1000 psi and 500 psi. The formulation ingredient amounts and evaluation results are given below in Table VII and Table VIII, respectively. Examples I and II of WO99/33437 are reproduced herein as Comparative Example 1 and Comparative Example 2, respectively.

EXAMPLES 7–8

To show the advantage of oral care tablets prepared according to the present invention as compared to those made in Comparative Example 1 and 2, tablets were formed from the same ingredients as in Comparative Examples 1 and 2, except a combination of calcium metasilicate and disintegration aid were added as partial ("A" Tablets) and total replacement ("B" Tablets) for the prescribed abrasive. Example 7 is made from the same formulation ingredients as Comparative Example I. For Tablets 7A, about one-half of the calcium carbonate abrasive was replaced with a combination of Example 1 calcium metasilicate and sodium starch glycolate disintegration aid. For Tablets 7B, all of the calcium carbonate abrasive was replaced with a combination of Example 1 calcium metasilicate and sodium starch glycolate disintegration aid.

Example 8 is made from the same formulation ingredients as Comparative Example II. For Tablets 8A, about one-half of the silica abrasive was replaced with a combination of Example 1 calcium metasilicate and sodium starch glycolate disintegration aid. For Tablets 8B, all of the silica abrasive was replaced with a combination of Example 1 calcium metasilicate and sodium starch glycolate disintegration aid. The exact formulation amounts for Example 7 and 8 are given below in Table VII.

Ingredients were mixed together as described in previous examples and tablets were formed by pressing the resulting mixture in an Angstrom press fitted with a 13-mm die at 2000 psi, 1000 psi and 500 psi.

TABLE VII

| | Comparative Ex. 1 | Tablet 7A | Tablet 7A | Comparative Ex. 2 | Tablet 8A | Tablet 8B |
|---|---|---|---|---|---|---|
| Sorbitol, g | — | — | — | 10 | 10 | 10 |
| Mannitol, g | 47 | 47 | 47 | 46.7 | 46.7 | 46.7 |
| Calcium Carbonate HUBERCAL ® 500 | 27 | 12 | 0 | — | — | — |
| Precipitated Silica, g ZEODENT ® 119 | — | — | — | 30 | 15 | 0 |
| Ex. 1 calcium metasilicate, g | — | 13.5 | 24.3 | — | 13.5 | 27 |
| Sodium Starch Glycolate, g | — | 1.5 | 2.7 | — | 1.5 | 3 |
| Pregelled Starch, g | 0.5 | 0.5 | 0.5 | — | — | — |
| Sodium lauryl sulfate, g | 1 | 1 | 1 | 1 | 1 | 1 |
| Potassium citrate, g | 2.1 | 2.1 | 2.1 | 1 | 1 | 1 |
| Sodium saccharine, g | — | — | — | 0.13 | 0.13 | 0.13 |
| Aspartame, g | 0.35 | 0.35 | 0.35 | — | — | — |
| Xanthan gum, g | 2.85 | 2.85 | 2.85 | 0.1 | 0.1 | 0.1 |
| Titanium Dioxide, g | 0.5 | 0.5 | 0.5 | — | — | — |
| Sodium CMC, g | 2.65 | 2.65 | 2.65 | 0.15 | 0.15 | 0.15 |
| Silica thickener, g ZEODENT ® 165 | 0.2 | 0.2 | 0.2 | 4.6 | 4.6 | 4.6 |
| Sucrose, g | 10 | 10 | 10 | — | — | — |

TABLE VII-continued

| | | | | | | |
|---|---|---|---|---|---|---|
| Magnesium stearate, g | 2.5 | 2.5 | 2.5 | 2.5 | 2.5 | 2.5 |
| Talc, g | 2 | 2 | 2 | 2 | 2 | 2 |
| Compression Force | Tablet Hardness, kP | | | | | |
| 2000 psi | 2.5 | 2.8 | 3 | 5.1 | 4.1 | 3.4 |
| 1000 psi | 1.1 | 1.5 | 1.5 | 3 | 2.8 | 2 |
| 500 psi | 1.4 | 1.4 | 1.8 | 2.2 | 1.8 | 1.3 |

Results for tablet hardness at the three compression forces used for each formulation are given in Table VII above. For each formulation, tablet hardness expressed in kP is measured on 3 tablets utilizing a Erweka TBH30 instrument (Milford, Conn.) and the results reported is an average of 3 measurements.

The oral care tablets prepared as described above in Comparative Examples 1 and 2 and Examples 7 and 8 from the formulations listed in Table VII were evaluated for disintegration according to the following procedure. Disintegration time was determined on Comparative Example 1, Tablets 7A and 7B compressed at 1000 psi and on Comparative Example 2, Tablets 8A and 8B compressed at 500 psi. Disintegration time was determined by placing 3 tablets in separate chambers in an Erweka ZT72 disintegrator (Milford, Conn.). The tablets were repeatedly immersed in 37° C. deionized water at a rate of 30 strokes/minute until the tablets disintegrated, as detected and recorded by the instrument. Results are given in Table VIII.

TABLE VIII

| | Disintegration Time, min:sec |
|---|---|
| Comparative Ex. 1 | 17:8 |
| Tablet 7A | 16:23 |
| Tablet 7B | 13:05 |
| Comparative Ex. 2 | 9:45 |
| Tablet 8A | 1:27 |
| Tablet 8B | 0:57 |

Tablets containing the inventive calcium metasilicate and disintegration aid (Tablets 7A, 7B, 8A and 8B) showed an improvement in disintegration time as compared to the comparative examples. Tablets 8A and 8B showed significant improvement in disintegration time over the prior art tablets. Of course, disintegration time could be improved further by optimizing the formulation as is shown in previous Examples 2–6.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An toothpaste comprising a calcium metasilicate having A aspect ratio (average major axial diameter/average minor axial diameter) of from about 1:1 to about 2.5:1, and an oil absorption of from about 20 ml/100 g to about 220 ml/100 g.

2. The toothpaste according to claim 1, wherein the calcium metasilicate has a $CaO/SiO_2$ molar ratio of 0.75 to 1.3.

3. The toothpaste according to claim 1, wherein the calcium metasilicate has a $CaO/SiO_2$ molar ratio of 0.95 to 1.05.

4. The toothpaste according to claim 1, wherein the calcium metasilicate is dehydrated.

5. The toothpaste according to claim 1, wherein the calcium metasilicate is wollastonite having a monoclinic crystal habit.

6. The toothpaste according to claim 1, wherein the calcium metasilicate is amorphous.

7. The toothpaste according to claim 1, further comprising one or more ingredients selected from the group consisting of: organoleptic enhancing agents, abrasives, disintegration aids, preservatives, therapeutic agents and thickening agents.

8. The toothpaste according to claim 7, wherein the organoleptic enhancing agent comprises one or more ingredients selected from the group consisting of humectants, sweeteners, flavorants, surfactants, colorants and effervescent agents.

9. An toothpaste comprising:
a calcium metasilicate having A aspect ratio (average major axial diameter/average minor axial diameter) of from about 1:1 to about 2.5:1, and an oil absorption of from about 20 ml/100 g to about 220 ml/100 g;
a disintegration aid; and
an organoleptic enhancing agent.

10. The toothpaste of claim 9, wherein the oral care composition further comprises one or more ingredients selected from the group consisting of thickening agents, therapeutic agents, sweeteners, preservatives, and abrasives.

11. The toothpaste of claim 9, wherein the organoleptic enhancing agent comprises one or more ingredients selected from the group consisting of humectants, sweeteners, flavorants, surfactants, colorants and effervescent agents.

* * * * *